United States Patent [19]

Spery

[11] Patent Number: 4,805,604
[45] Date of Patent: Feb. 21, 1989

[54] RECEPTIVE CONDOM

[76] Inventor: Nanette S. Spery, 880 W. 181st St., New York, N.Y. 10033

[21] Appl. No.: 169,391

[22] Filed: Mar. 9, 1988

Related U.S. Application Data

[63] Continuation-in-part of Ser. No. 33,796, Jun. 15, 1987, abandoned.

[51] Int. Cl.⁴ ............... A61F 5/00; A61F 13/00; A61F 5/44; A61B 19/00
[52] U.S. Cl. ..................... 128/79; 604/347; 128/830; 128/844
[58] Field of Search ............ 128/79, 127, 130, 132 R, 128/132 D, 129; 604/347, 348, 349

[56] References Cited

U.S. PATENT DOCUMENTS

| | | | |
|---|---|---|---|
| 3,452,749 | 7/1969 | Riedell | 128/130 |
| 3,495,589 | 2/1970 | Clement | 128/79 |
| 3,512,528 | 5/1970 | Whitehead et al. | 128/129 |
| 3,631,857 | 1/1972 | Maddison | 604/349 |
| 3,820,533 | 6/1974 | Jones | 604/349 |
| 4,275,812 | 6/1981 | Poncy et al. | 128/132 R |
| 4,281,648 | 8/1981 | Rogers | 128/79 |
| 4,354,494 | 10/1982 | Hogin | 128/132 R |

Primary Examiner—Robert A. Hafer
Assistant Examiner—Michael Brown
Attorney, Agent, or Firm—Darby & Darby

[57] ABSTRACT

This invention is in the field of contraception, and relates also to the prevention of the transmission of venereal diseases. The invention relates to a condom adapted to be received by a passive sexual organ prior to intercourse. The condom comprises a thin elastic membrane sheath having a closed end, a supporting ring structure at its open end, and an insertion tube adapted to deliver the condom to a passive sexual organ, such as the vaginal cavity, prior to intercourse and without first affixing the condom to an erect penis.

10 Claims, 2 Drawing Sheets

RECEPTIVE CONDOM

This application is a continuation-in-part of application Ser. No. 033,796 now abandoned.

This invention relates to the field of contraception and to the control of venereal disease transmission, including Acquired Immune Deficiency Syndrome (AIDS) and Human Immunodeficiency Virus (HIV) infection.

BACKGROUND OF THE INVENTION

Four basic types of female contraceptives are known. There are orally administered pharmaceuticals; the cervical cap; devices which rely on chemical spermicides, such as diaphragms, sponges, foams, jellies, and suppositories; and the Intrauterine Device.

All of these contraceptives suffer from serious disadvantages. Although effective in preventing conception, oral contraceptives reportedly have various undesirable side effects, including possible implication in carcinogenic damage to the gall bladder and liver. The diaphragm, while reliable when correctly used, is a cumbersome and inconvenient contraceptive that can easily interrupt or detract from the act of intercourse. Spermicidal contraceptives are also inconvenient to use and may be only as much as 85% reliable as a contraceptive. The cervical cap cannot be fitted on some women, and on women who are able to wear it, it may produce discomfort and infection. The intrauterine device has been the subject of much public controversy, and has been reported to be unsafe under certain circumstances.

There may also be a possibility of danger to women who are susceptible to Toxic Shock Syndrome, since the cervical cap, the intrauterine device and spermicidal implants are all foreign bodies that are left inside the vaginal vault either permanently or for several hours after intercourse.

None of the known methods of female contraception provide adequate and independent protection from sexually transmitted diseases. Although spermicidal implants may provide some protection, the available female contraceptives do not provide a reliable impermeable barrier to infection vectors, such as viruses, microbes, etc.

Unlike female contraceptives, the male condom is the only reversible form of contraceptive available to men. It is also the most reliable protection against sexually transmitted disease that is currently available to either sex—even though the male condom may have a failure rate as high as 17%. The male condom, especially when made of latex, provides an effective membrane barrier against the transmission of infection.

Advantages of the present male condom are that it does not normally cause any side effects to either partner. It is widely available, economical, and does not require a doctor's services.

The male condom has several disadvantages, such as breakage, leakage, and slippage. In addition, the penis must be erect in order to put on the condom, which causes an untimely interruption of the sex act. After ejaculation, if the penis is left inside and continues to soften, the conventional condom may slip off, causing unwanted leakage of semen and infectious matter. In addition, a loss of sensation can be caused by the fact that the present male condom must often be tight-fitting in order to stay in place. Another disadvantage of the male condom is that it places the responsibility for contraception and disease prevention primarily on one partner.

The present male condom comprises an elongated tubular sheath made of thin, flexible material such as latex film. The sheath is closed at one end and open at the other end to provide for the insertion of a penis. The opening includes a periphery having a beaded or constricted rim. The condom is put on by rolling it onto or pulling it onto an erect penis. The latex-type type condom fits tightly in order to be kept in place during intercourse.

SUMMARY OF THE INVENTION

The receptive condom according to the invention is a condom adapted to be worn by the sexually passive partner, (e.g., the female) comprising a thin elastic sheath that is closed at one end and open at the other and which has a generally phallic shape. The sheath is sized to fill and line the passive sexual organ of the passive partner, receive a penis at the open end, yield to a penis within the passive sexual organ, and enclose without actively gripping the penis. Within the context of this invention, a passive sexual organ is any organ which receives an erect penis during sexual relations (e.g., intercourse). The sheath is provided with a cushioning outer ring of soft, smooth rubber at the open end. The outer cushioning ring surrounds a thin, inflexible (but not hard) rubber inner ring, which fits on the outside of the opening of a passive sexual organ. The purpose of the inflexible inner ring is to provide rigidity, so that the soft rubber outer ring does not fold or buckle and get pushed or pulled inside the passive sexual organ during sexual relations. The receptive condom sheath and ring may also be sized for comfort, for example within a range of at least five sizes—petite, small, medium, large, and extra large. The size needed is determined by the size of the opening of the passive sexual organ.

The invention also provides a means for inserting the condom sheath, closed end first, but not the dual-ring structure, into the passive sexual organ of a passive partner. The preferred insertion means incorporates an insertion tube (preferably of glazed cardboard) and a charge of compressed air, in communication with the inside of the condom. The tube and charge are adapted to impart temporary forward momentum and rigidity to the condom sheath under pressure, so that the sheath is forced out of the tube and into the passive sexual organ, closed end first. The collapsed charge and attached tube are then easily removed, leaving the condom in place inside the passive sexual organ. The double ring structure (previously described) prevents the receptive condom from being pushed completely into the passive organ. The condom can be lubricated or not, as desired. It can also be individually wrapped in tamper-proof, sanitary packaging. As an alternative to compressed air, a plunger-type arrangement could be used, although compressed air is preferred for convenience and to minimize any threat to the integrity of the condom body during insertion into a passive sexual organ.

There are numerous advantages achieved by the receptive condom when compared to conventional condoms and methods of birth control. There is no loss of spontaneity, as the receptive condom can be inserted before foreplay begins. Since the dual ring structure remains on the outside of the sexual orifice, without gripping the penis, the penis may remain inside and grow soft, with no danger of slipping of the condom or subsequent leakage. The receptive condom may also be left in place for a repeat performance, if desired but repeated usage is generally not recommended. The receptive condom does not have to fit the penis tightly, and therefore loss of sensation is reduced.

Other advantages include an increased responsibility for birth control by the woman. Also, the invention is economical, and is comparable in cost to conventional male condoms. Similarly, the receptive condom does not require a visit to a clinic or doctor's office.

Protection from sexually transmitted diseases can be improved over the 17% failure rate of the present male condom, because the problems of slipping, falling off, and leakage may be rectified by the external ring of the invention, by the looser fit, and by the reduced stress which the receptive condom incurs.

The receptive condom may include but does not require the use of chemical spermicides or anti-disease medication. Like conventional condoms, the invention can be removed after intercourse (unlike the sponge or diaphragm, which must be left in for 6 to 8 hours in order to be effective)—a definite advantage to women who are susceptible to Toxic Shock Syndrome.

These and other advantages and objectives of the invention will be apparent from the following description and drawings.

DETAILED DESCRIPTION

Figure 1:
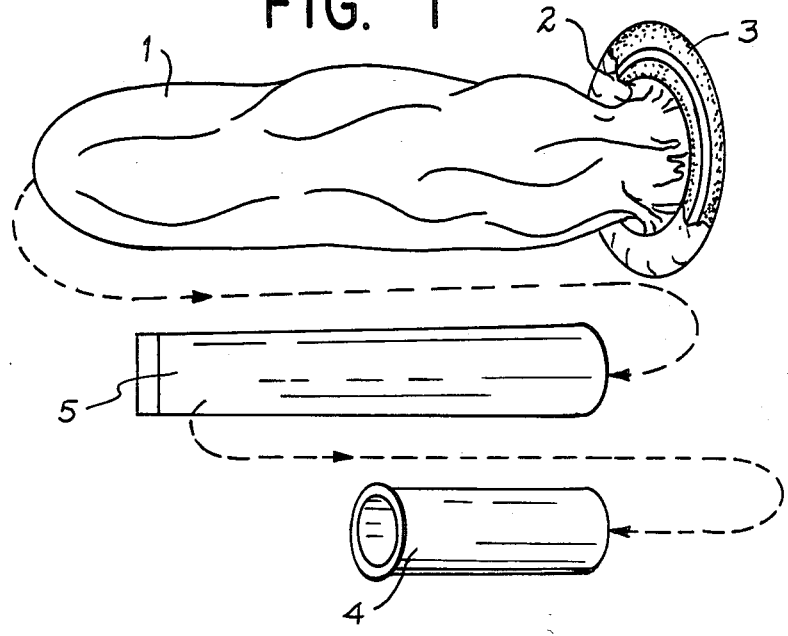
FIG. 1 shows a side view of the unassembled receptive condom.

Referring to FIG. 1, the invention comprises a condom body 1 with inner ring 2 and outer ring 3. The condom body 1 is generally phallic in shape, and is closed at one end. The rings 1 and 2 are affixed to the open end. The condom body may be constructed of latex film materials, natural lamb ceca products, or other materials suitable for use as a condom body. The body 1 is larger than that of conventional male condoms, so that when the receptive condom is fully open and extended is will surround but not actively grip an erect penis.

The body of the condom 1, before use, is assembled into a storage and insertion housing, comprising an insertion tube 4 and an applicator means. In the embodiment shown, the discharged tube 5 comprises a canister for compressed air.

Figure 2:
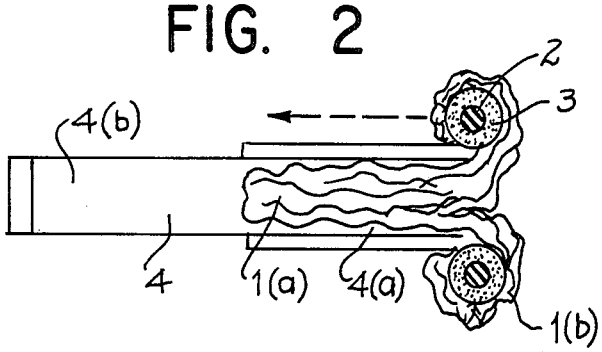
FIG. 2 is a cut-away view in partial cross section, showing the assembled receptive condom in its storage condition.

As shown in FIG. 2, the condom body is placed closed-end first into an open-ended insertion tube 4, so that a front portion 1(a) of the condom body 1 resides within a front portion 4(a) of the insertion tube 4. A rear portion (1d) of the condom body 1 extends outside the front portion 4(a) of the insertion tube 4, and is rolled up around the rings 2 and 3. In this way, the front end of the insertion tube 4 is sealed closed by the condom body 1. Also, this construction provides an additional sanitary measure and is more convenient for storage and handling.

The front portion 1(a) of the condom body 1 remains relatively loose within the insertion tube 4. It is important that the condom body 1 be inserted as a uniform phallic shape, albeit a flaccid one, without stuffing or bunching, in order to ensure that it can be freely removed from the insertion tube 4 and properly inserted into a passive sexual organ. Although not shown, the condom body could be partially and temporarily inflated, in order to more conveniently place the front portion 1(a) within the insertion tube 4.

The insertion tube 4 also has a rear portion 4(b) extending away from the condom body 1 and its enclosed front portion 1(a). The portion 4(b) terminates in an open end that is adapted to receive an applicator means, such as a plunger arrangement or a canister of compressed air. (Not shown). In some circumstances, the insertion tube 4 can itself serve as the applicator means. In a preferred embodiment, the insertion tube 4 is made of stiff glazed cardboard.

The rings 2 and 3, with half the condom body rolled around it, is at the other end of a conventional sanitary package (not shown) from the applicator means, until just before insertion. The receptive condom can be stored in this manner until ready for use.

Figure 3:
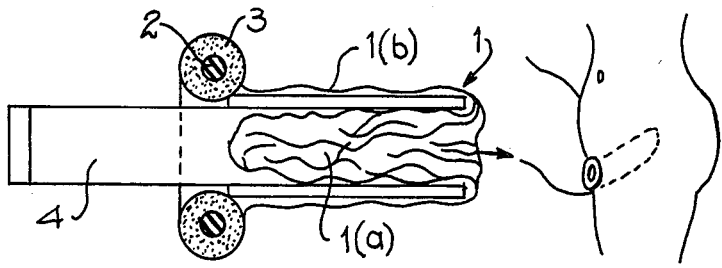
FIG. 3 is the same view as in FIG. 2, showing the assembled receptive condom just prior to insertion in a passive sexual organ.

When the receptive condom is ready for use, and the sanitary packaging is removed, the rings 2,3 and the rear portion 1(b) of condom body 1 are pulled backward around the insertion tube 4, FIG. 3. In this way, the portion 1(b) becomes unrolled, and surrounds the outside of the front portion 4(a) of the insertion tube 4, while the front portion 1(a) of the condom body 1 remains inside the front portion 4(a) of the insertion tube 4. This provides additional sanitary protection, since, as will be seen, the passive sexual organ will come in contact only with the condom body 1, and not with the insertion tube 4 itself. When the receptive condom is inserted with compressed air, it is important that the seal between the condom body 1(b) and the front end of the insertion tube 4 be maintained until insertion.

Figure 4:
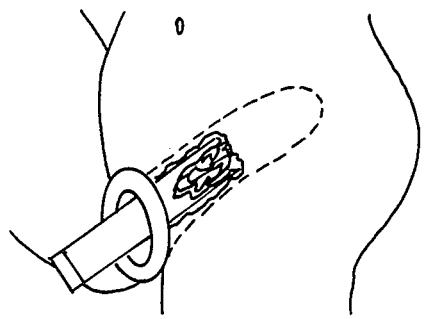
FIGS. 4 through 6 are schematic cut-away views showing the insertion of the condom into a passive sexual organ.
Figure 5:
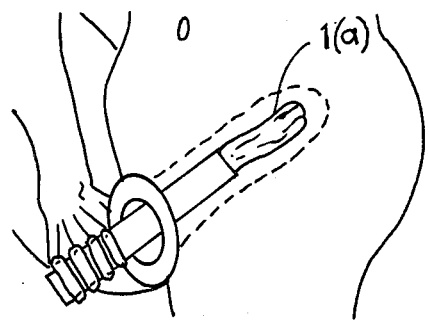
Figure 6:
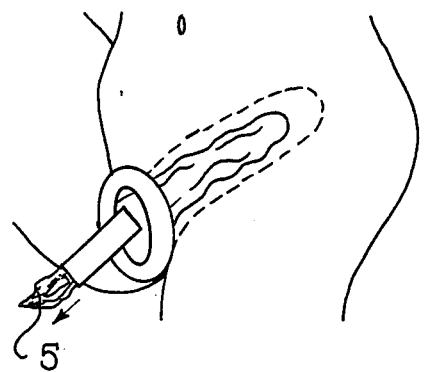

The assembly is now ready for positioning inside a passive sexual organ, as shown in FIGS. 4–6.

First, the assembly shown in FIG. 3 is inserted into the opening of a passive sexual organ front-end first, until the rings 2,3 prevent any further forward motion, FIG. 4. Thus, the rings 2,3 are always on the outside of the passive sexual organ. Next, an applicator means 5 is used to discharge the front portion 1(a) of the condom body 1 from the front end of insertion tube 4, so that the entire condom body 1 is inside the passive sexual organ, while the rear portion 1(b) of the condom body 1 continues to surround the front portion 4(a) of the insertion tube 4. FIG. 5. Finally, as shown in FIG. 6, the insertion tube 4 is removed, leaving the receptive condom in place inside a passive sexual organ, and ready to receive a penis.

The preferred applicator means 5, as represented for example in FIG. 6, is a canister or charge of compressed air. Other suitable application means could also be used, such as a mechanical plunger arrangement. In theory, compressed air is preferred, because it poses less of a threat to the integrity of the condom body and provides a more convenient "one-step" application. The compressed air discharges the condom body 1 from insertion tube 4 and into the passive sexual organ. It is not believed necessary to actually inflate the condom to achieve this result.

I CLAIM

1. A condom adapted to be received by a passive sexual organ comprising a thin, uniform elastic sheath having a closed end, an open end, and which has a generally phallic shape, said sheath being sized to selectively receive and enclose, without actively gripping, a male sexual organ via said open end, and said sheath having a front portion proximate to said closed end and a rear portion proximate to said open end, an outer flexible ring circumferentially affixed to the open end of said sheath, said outer ring containing a thin, inflexible inner ring, the two ring combination having an internal diameter adapted to receive and guide the male sexual organ into said sheath, without actively gripping said male sexual organ, and a selectively removable insertion tube having an open front end, said insertion tube having a housing portion which extends from the open front end of said tube, surrounds the front portion of said sheath, and at least a part of which housing portion of said insertion tube is surrounded by at least one of said outer ring and at least a part of said rear portion of said sheath, said sheath comprising a circumferential seal at the open front end of said insertion tube, where the front and rear portions of said sheath meet.

2. A condom as in claim 1, additionally comprising an applicator means for discharging said sheath from said insertion tube.

3. A condom as in claim 2, wherein the condom body and the insertion tube are of substantially the same length.

4. A condom as in claim 2, wherein the diameter of the insertion tube is less than the diameter of the inner ring.

5. A condom as in claim 2, wherein said applicator means comprises a charge of compressed air.

6. A condom as in claim 2, wherein said applicator means comprises a plunger.

7. A condom as in claim 3, wherein the charge of compressed air is in airtight coaxial communication with said insertion tube.

8. A condom as in claim 2, wherein said sheath is made from a material selected from the group consisting of latex film materials and natural lamb cecum products, said outer ring is made of a soft flexible rubber material, and said inner ring is made of a thin, inflexible, rubber material.

9. A condom adapted to be received by a passive sexual organ comprising a thin, uniform elastic sheath having a closed end, an open end, and which has a generally phallic shape, said sheath being sized to selectively receive and enclose, without actively gripping, a male sexual organ via said open end, and said sheath having a front portion proximate to said closed end and a rear portion proximate to said open end, an outer flexible ring circumferentially affixed to the open end of said sheath, said outer ring containing a thin, inflexible inner ring, the two ring combination having an internal diameter adapted to receive and guide the male sexual organ into said sheath, without actively gripping said male sexual organ, a selectively removable insertion tube having a rear end and an open front end, said insertion tube having a housing portion which extends from the open front end of said tube, surrounds the front portion of said sheath, and at least a part of which housing portion of said insertion tube is surrounded by at least one of said outer ring and at least a part of said rear portion of said sheath, said sheath comprising a circumferential seal at the open front end of said insertion tube, where the front and rear portions of said sheath meet, and a charge of compressed air in airtight coaxial communication with the rear end of said insertion tube and confronting said front portion of said sheath.

10. A condom as in claim 9, wherein the condom body and the insertion tube are of substantially the same length and the diameter of the insertion tube is less than the diameter of the inner ring.

* * * * *